(12) United States Patent
Chen et al.

(10) Patent No.: US 9,233,925 B2
(45) Date of Patent: Jan. 12, 2016

(54) PROCESS FOR PREPARATION OF ROFLUMILAST

(71) Applicant: SCINOPHARM (CHANGSHU) PHARMACEUTICALS, LTD., Changshu, Jiangsu Province (CN)

(72) Inventors: Yi-Jing Chen, Meishan Township (TW); Stanislaw Pikul, East Windsor, NJ (US); Shen-Chun Kuo, Union, NJ (US); Guo-dong Chu, Jiaxiang County (CN)

(73) Assignee: ScinoPharm (Changshu) Pharmaceuticals, Ltd., Changshu, Jiangsu (CN)

( * ) Notice: Subject to any disclaimer, the term of this patent is extended or adjusted under 35 U.S.C. 154(b) by 0 days.

(21) Appl. No.: 14/736,062

(22) Filed: Jun. 10, 2015

(65) Prior Publication Data
US 2015/0274667 A1    Oct. 1, 2015

Related U.S. Application Data

(62) Division of application No. 14/382,967, filed as application No. PCT/CN2013/072286 on Mar. 7, 2013, now Pat. No. 9,085,533.

(30) Foreign Application Priority Data

Mar. 7, 2012  (CN) ................ PCT/CN2012/072020

(51) Int. Cl.
| | |
|---|---|
| *C07D 213/74* | (2006.01) |
| *C07D 213/75* | (2006.01) |
| *C07C 43/315* | (2006.01) |
| *C07C 43/205* | (2006.01) |
| *C07C 43/307* | (2006.01) |
| *C07D 317/22* | (2006.01) |
| *C07D 319/06* | (2006.01) |

(52) U.S. Cl.
CPC .......... *C07D 213/74* (2013.01); *C07C 43/2055* (2013.01); *C07C 43/307* (2013.01); *C07C 43/315* (2013.01); *C07D 213/75* (2013.01); *C07D 317/22* (2013.01); *C07D 319/06* (2013.01)

(58) Field of Classification Search
CPC .................................................... C07D 213/74
USPC ........................................................ 546/312
See application file for complete search history.

(56) References Cited

U.S. PATENT DOCUMENTS 5,712,298 A    1/1998    Amschler

FOREIGN PATENT DOCUMENTS

| CN | 102336703 A | 2/2012 |
|---|---|---|
| CN | 102351787 A | 2/2012 |
| WO | 93/25517 A1 | 12/1993 |
| WO | 94/02465 A1 | 2/1994 |
| WO | 95/01338 A1 | 1/1995 |
| WO | 2004/033430 A2 | 4/2004 |
| WO | 2004/080967 A1 | 9/2004 |
| WO | 2008/006509 A1 | 1/2008 |

OTHER PUBLICATIONS

Evans et al., "Enantioselective Synthesis of Oasomyein A, Part I: Synthesis of the C1-C12 and C13-C28 Subunits," Angew. Chem. Int. Ed., 2007, vol. 46, pp. 537-540.
Mohamed et al., "Accessing the amide functionality by the mild and low-cost oxidation of imine," Tetrahedron Letters, Feb. 2009, vol. 50, pp. 3436-3438.
International Search Report and Written Opinion Corresponding to. PCT/CN2013/072286 mailed Jun. 13, 2013, 7 pages.
International Search Report Corresponding to PCT/CN2012/072020, mailed Dec. 13, 2012; 6 pages.

*Primary Examiner* — Patricia L Morris
(74) *Attorney, Agent, or Firm* — Kilpatrick Townsend & Stockton LLP

(57) ABSTRACT

The present invention provides novel processes for the preparation of N-substituted benzamides having the formula VIc:

[Structure VIc: benzamide with $R^1O$ and $R^2O$ substituents connected via amide linkage to a dichloropyridine]

In some embodiments, the invention provides a process for preparation of roflumilast and other pharmaceutically active species. Novel compounds, including intermediates for the synthesis of roflumilast, are also provided.

3 Claims, 1 Drawing Sheet

PROCESS FOR PREPARATION OF ROFLUMILAST

CROSS-REFERENCES TO RELATED APPLICATIONS

This application claims priority from International application Serial Number PCT/CN2012/072020, filed on Mar. 7, 2012, the entire content of which is hereby incorporated by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Phosphodiesterases (PDEs) are a family of enzymes that metabolize 3',5' cyclic nucleotides to 5' nucleoside monophosphates, thereby regulating the activity of second messengers such as cyclic adenosine monophosphate (cAMP) and cyclic guanosine monophosphate (cGMP). Phosphodiesterase type 4 (PDE4), which is a subfamily of cAMP-specific PDE, has generated interest as a target for the development of novel anti-asthmatic and anti-inflammatory compounds. PDE4 is known to exist in at least four isoforms, each of which is encoded by a distinct gene. Each of the four known PDE4 gene products is believed to play varying roles in over forty allergic and/or inflammatory responses. Inhibition of PDE4, and in particular the inhibition of specific isoforms that produce detrimental responses, can beneficially affect allergy and inflammation symptoms. Practical and economical methods providing novel PDE4 inhibitors are therefore highly desirable.

Roflumilast (CAS 162401-32-3) is a member of a class of fluoroalkoxy-substituted benzamides developed by BYK Gulden Lomberg Chemische Fabrik GmbH (see, for example, U.S. Pat. No. 5,712,298). The chemical name of roflumilast is 3-(cyclopropylmethoxy)-N-(3,5-dichloro-pyridin-4-yl)-4-(difluoromethoxy) benzamide. The compound is indicated to be useful as a PDE4 inhibitor.

WO 95/01338 describes the preparation of dialkyl-substituted benzamides, including roflumilast, and the use thereof as PDE4 inhibitors. Such compounds are also proposed for the treatment of certain disorders of the skin such as dermatoses. WO 2004/033430 describes the preparation of a dialkoxy-substituted benzoyl compound which can be further converted to dialkoxy-substituted benzamides.

WO 94/02465 and WO 93/25517 describe the preparation of dialkoxy-substituted benzamides. The compounds are obtained by reacting activated benzoic acid derivatives of the general formula:

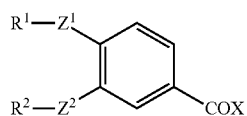

with amines of the general formula $R^3NH_2$. The disclosed benzoic acid derivatives are acid halides, especially acid chlorides, and anhydrides. The reaction takes place in the presence of a base (e.g. an organic base such as triethylamine, N-methylmorpholine, or pyridine; or an alkali metal hydride, such as sodium hydride) in an inert solvent.

WO 2004/080967 describes the preparation of dialkoxy-substituted benzamides from dialkoxy-substituted benzoic acid and the anion of 4-amino-3,5-dichloropyridine. Roflumilast is prepared using the anion of 4-amino-3,5-dichloropyridine (Scheme 1, Formula 1, below) and an activated derivative of 3-cyclopropylmethoxy-4-difluoromethoxybenzoic acid that contains a suitable leaving group (Scheme 1, Formula 2, below). The use of a strong base, such as KO$^t$Bu, NaO$^t$Bu, or LiO$^t$Bu, is necessary to prepare the anion 1, and the reaction temperature must be maintained between 15 and 30° C. The preparation of benzoic acid derivative 2, where LG is a chloride leaving group, requires 1-4 equivalents of thionyl chloride for reaction with 3-cyclopropylmethoxy-4-difluoromethoxybenzoyl acid at 70-90° C. The coupling of 1 and 2 is carried out at 20-30° C. in DMF.

Scheme 1

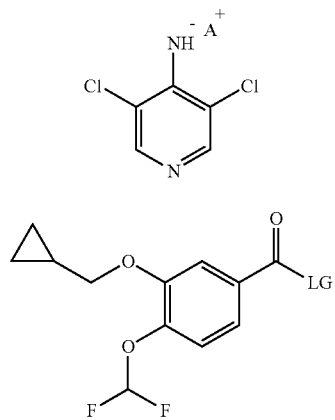

WO 2004/033430 describes the preparation of a dialkoxy-substituted benzoyl compound which can be further converted to dialkoxy-substituted benzamides, including roflumilast, using carbonylation technology. The key intermediates, including 3-cyclopropyl methoxy-4-difluoromethoxybenzoic acid and its derivatives (as disclosed in WO 2004/080967), are derived via carbonylation of 1-halo-3-cyclopropylmethoxy-4difluoromethoxybenzene.

Although processes for roflumilast preparation have been disclosed as discussed above, none of the known methods are environmentally friendly. The known processes are either environmentally harmful or used in harsh conditions. WO 95/01338, for example, describes the preparation of dialkyl-substituted benzamides by making use of thionyl chloride, which is corrosive, explosive and may produce dangerous gases such as sulfur dioxide, and pyrophoric strong bases such as sodium hydride. Meanwhile, WO 2004/080967 describes the preparation of roflumilast by using combustible potassium tert-butoxide (KO$^t$Bu). Accordingly, there remains an unmet need for a simple and safe process for industrial preparation of roflumilast and similar benzamides. The practical and economical processes disclosed herein address this need and other needs.

BRIEF SUMMARY OF THE INVENTION

In one aspect, the present invention provides a process for the preparation of a compound of formula VIc:

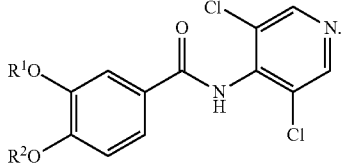
VIc

The process includes:
a) converting a compound of formula Vc

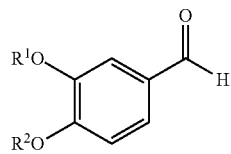
IIc to a compound of formula Vc

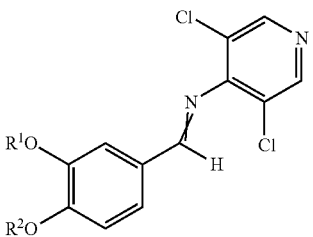
Vc in a one-pot reaction; and
b) oxidizing the compound of formula Vc under conditions suitable to provide the compound of formula VIc; wherein $R^1$ and $R^2$ are independently selected from the group consisting of H; $C_{1-6}$ alkyl; $C_{3-7}$ cycloalkyl; $C_{3-7}$ cycloalkylmethyl; and $C_{1-4}$ alkyl which is partially or completely substituted with fluorine.

In a second aspect, the present invention provides a compound of formula Vc

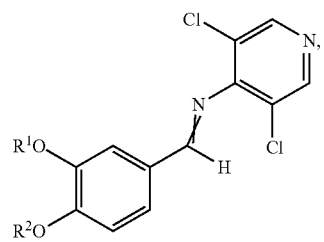
Vc wherein the 'crossed' imine bond indicates cis, trans or a mixture of cis and trans isomers, as well as a compound of formula IIIc

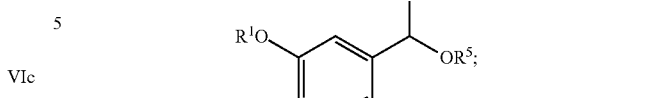
IIIc wherein:
$R^1$ and $R^2$ are independently selected from the group consisting of H; $C_{1-6}$ alkyl; $C_{3-7}$ cycloalkyl; $C_{3-7}$ cycloalkylmethyl; and $C_{1-4}$ alkyl which is partially or completely substituted with fluorine; and $R^4$ and $R^5$ are independently selected from the group consisting of $C_{1-6}$ alkyl and acyl; or $R^4$ and $R^5$ are taken together to form an optionally substituted 5-7 member cyclic ring.

In a third aspect, the present invention provides a process for the preparation of a compound of structure VIc

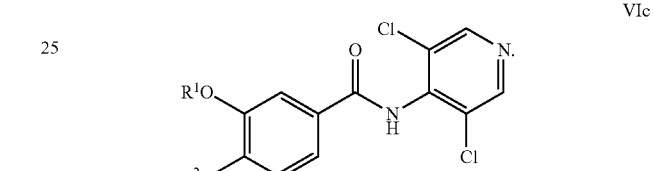
VIc

The process includes:
a) contacting a compound of formula IIc

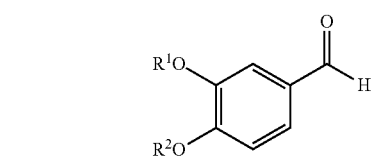
IIc with a compound of formula IVa

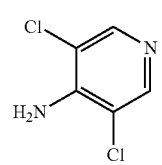
IVa under conditions sufficient to provide a compound of formula Vc

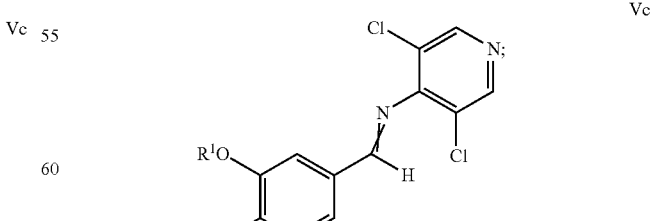
Vc and
b) oxidizing the compound of formula Vc under conditions suitable to provide the compound of formula VIc;

wherein
R¹ and R² are independently selected from the group consisting of H; $C_{1-6}$ alkyl; $C_{3-7}$ cycloalkyl; $C_{3-7}$ cycloalkylmethyl; and $C_1$ alkyl which is partially or completely substituted with fluorine.

DETAILED DESCRIPTION OF THE INVENTION

I. General

Figure 1:
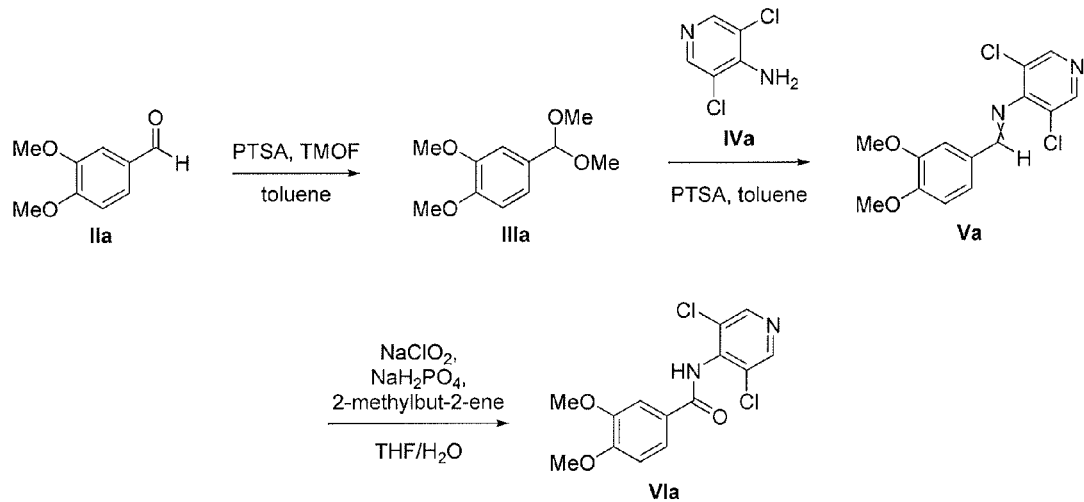
FIG. 1 shows the schematic for the synthesis of N-(3,5-dichloro-pyridin-4-yl)-3,4-dimethoxy-benzamide from 3,4-dimethoxybenzaldehyde.

The present invention provides a process for preparation of substituted benzamides from substituted benzaldehydes. The novel one-pot methods have been discovered to be mild, safe, economically efficient, and environmentally friendly. The inventive process eliminates the need for caustic or dangerous reagents such as thionyl chloride and sodium hydride.

II. Definitions

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

As used herein, the term "alkyl" by itself or as part of another substituent, means, unless otherwise stated, a straight or branched chain hydrocarbon radical. Alkyl substituents, as well as other hydrocarbon substituents, may contain number designators indicating the number of carbon atoms in the substituent (i.e. $C_1$-$C_8$ means one to eight carbons), although such designators may be omitted. Unless otherwise specified, the alkyl groups of the present invention contain 1 to 12 carbon atoms. For example, an alkyl group can contain 1-2, 1-3, 1-4, 1-5, 1-6, 1-7, 1-8, 1-9, 1-10, 1-11, 1-12, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

As used herein, the term "acyl" refers to an alkyl radical as described above, wherein the carbon atom attached to the remainder of a molecule is substituted with an oxo group so as to form a C=O bond. Examples of acyl groups include, but are not limited to, acetyl, propionyl, and butyryl.

As used herein, the term "cycloalkyl" refers to an alkyl group as described above, wherein the carbon chain is a cyclic carbon chain. The cycloalkyl groups of the present invention contain at least 3 carbon atoms.

As used herein, the term "one-pot reaction" refers to a reaction in which a starting material undergoes at least two sequential chemical transformations in a single reaction vessel. In general, compounds formed as intermediates in the sequence are not isolated from a one-pot reaction mixture. Reagents necessary to affect the transformation sequence may be added together at the beginning of the sequence, or they may be added one after another as the sequence progresses.

As used herein, the term "protecting reagent" refers to a reagent capable of reacting with a functional moiety to form a protecting group that renders the functional moiety unreactive. The protecting group is also removable so as to restore the functional moiety to its original state. A protecting reagent can be an "aldehyde protecting reagent" wherein the protected functional moiety is an aldehyde. Such reagents are capable of reacting with aldehydes to form protecting groups including acetals, monothioacetals, dithioacetals, and hydrazones. Various protecting groups and protecting reagents, including aldehyde protecting reagents, are well known to one of ordinary skill in the art and include compounds that are disclosed in *Protective Groups in Organic Synthesis*, 4th edition, T. W. Greene and P. G. M. Wuts, John Wiley & Sons, New York, 2006, which is incorporated herein by reference in its entirety.

III. Embodiments of the Invention

The present invention provides a process for the preparation of substituted benzamides from substituted benzaldehydes. In one aspect, the invention provides a process for the preparation of a compound of formula VIc:

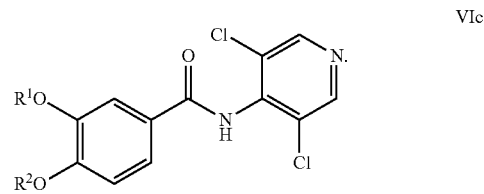

The process includes:
a) converting a compound of formula IIc

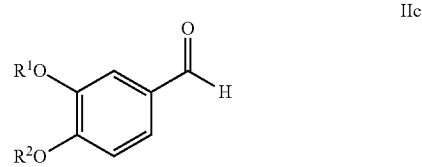

to a compound of formula Vc

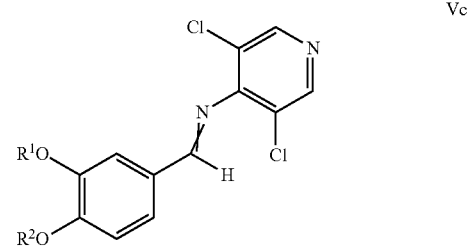

in a one-pot reaction; and
b) oxidizing the compound of formula Vc under conditions suitable to provide the compound of formula VIc;
wherein:
R¹ and R² are independently selected from the group consisting of H; $C_{1-6}$ alkyl; $C_{3-7}$ cycloalkyl; $C_{3-7}$ cycloalkylmethyl; and $C_{1-4}$ alkyl which is partially or completely substituted with fluorine.

Throughout the specification, the use of a crossed imine double bond is meant to indicate cis, trans, or a mixture of cis and trans orientations about the double bond.

In some embodiments, a substituted benzaldehyde IIc is activated by converting it to a substituted benzaldehyde acetal. The substituted benzaldehyde acetal then reacts with 4-amino-3,5-dichloropyridine providing a substituted phenyl imine. The substituted phenyl imine is then oxidized to provide a substituted benzamide. In some embodiments, the one-pot reaction of step a), discussed above, comprises:

i) converting a compound of formula (IIc) under conditions sufficient to provide a compound of formula (IIIc)

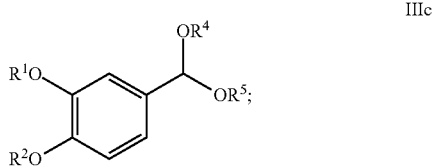

and ii) contacting the compound of formula IIIc with a compound of formula IVa

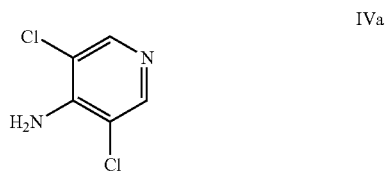

under conditions suitable to form the compound of formula Vc;

wherein:

R$^4$ and R$^5$ are independently selected from the group consisting of C$_{1-6}$ alkyl and acyl; or R$^4$ and R$^5$ are taken together to form an optionally substituted 5-7 member cyclic ring.

Preferably, the one-pot reaction converting IIc to Vc is conducted in a non-polar organic solvent under acidic conditions with or without an aldehyde protecting reagent. In some embodiments the invention provides a method for the preparation of a compound of formula VIc as described above, wherein: 1. the conversion of aldehyde IIc to benzacetal IIIc is conducted in a non-polar organic solvent in the presence of an acid; and 2. the one-pot conversion optionally includes an aldehyde protecting reagent. The organic solvent can be selected from suitable solvents including, but not limited to, toluene, xylene, and mixtures thereof. Acidic conditions can be maintained by using an acid such asp-toluenesulfonyl acid (PTSA), camphorsulfonic acid, acetic acid, and the like. In some embodiments the inventive process includes a one-pot reaction as described above, wherein the non-polar organic solvent is selected from the group consisting of toluene and xylene. In some embodiments the inventive process includes a one-pot reaction as described above, wherein the acid is selected from the group consisting of p-toluenesulfonic acid, camphorsulfonic acid, polymeric resin based sulfonic acid and acetic acid.

Any suitable aldehyde protecting reagent may be used in the methods of the present invention. Suitable reagents are capable of reacting with aldehydes to form protecting groups, including but not limited to acetals, monothioacetals, dithioacetals, and hydrazones. Such protecting groups can be removed to restore the aldehyde moiety. In some embodiments the inventive process includes a one-pot reaction as described above, wherein the aldehyde protecting reagent is selected from the group consisting of trimethyl orthoformate (TMOF), triethyl orthoformate, triethyl orthoacetate, trimethyl orthoacetate, acetic anhydride, ethylene glycol, and propylene glycol. One of skill in the art will appreciate that still other aldehyde protecting reagents may be useful in the inventive process.

The oxidative conversion of Vc to VIc can be conducted under any suitable conditions. In particular, the present invention provides a process for preparing substituted benzamides via imine oxidation using aqueous conditions requiring neither strong bases nor dangerous acid derivatives. The process is safe, energy efficient, and environmentally friendly. In some embodiments, benzamide oxidation is conducted using a mixture of tetrahydrofuran and water. In some embodiments the inventive process includes the oxidation of Vc as described above, wherein the oxidation step includes an oxidant selected from the group consisting of a chlorite, a transition metal catalyst, nickel peroxide, meta-chloroperoxybenzoic acid (m-CPBA), tert-butyl hydroperoxide (TBHP), potassium peroxomonosulfate (Oxone), or mixtures thereof. In some embodiments, the chlorite is selected from the group consisting of chlorous acid, magnesium chlorite, sodium chlorite, and potassium chlorite. The oxidation step can be conducted in a buffered solution. In some embodiments, the oxidation step is conducted with a chlorite that is buffered with an electrolyte selected from the group consisting of HCl/sodium citrate, citric acid/sodium citrate, acetic acid/sodium citrate, potassium dihydrogen phosphate, dipotassium phosphate/sodium dihydrogen phosphate, acetic acid, and disodium phosphate mixtures.

In some embodiments the present invention provides a process for preparing an N-substituted (3,4-dimethoxy)benzamide from a (3,4-dimethoxy)benzaldehyde, wherein the (3,4-dimethoxy)benzaldehyde is activated by converting it to a (3,4-dimethoxy)benzacetal (as shown, for example, in FIG. 1). The (3,4-dimethoxy)benzacetal then reacts with a substituted amine, resulting in an N-substituted (3,4-dimethoxy) benzylimine. The N-substituted (3,4-dimethoxy)benzylimine is then oxidized under conditions suitable to provide the N-substituted (3,4-dimethoxy)benzamide.

Figure 2:
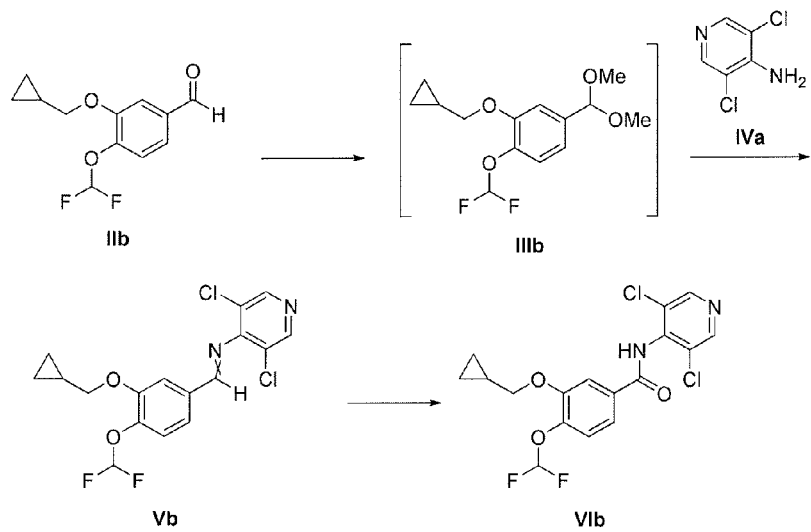
FIG. 2 shows the schematic for the synthesis of roflumilast from 3-cyclopropyl methoxy-4-difluoromethoxybenzaldehyde.

In some embodiments the present invention provides a process for preparing an N-substituted (3-cyclopropylmethoxy-4-difluoromethoxy)benzamide from a (3-cyclopropylmethoxy-4-difluoromethoxy)benzaldehyde, wherein the (3-cyclopropylmethoxy-4-difluoromethoxy)benzaldehyde is activated by converting it to a (3-cyclopropylmethoxy-4-difluoromethoxy)benzacetal (as shown, for example, in FIG. 2). The (3-cyclopropylmethoxy-4-difluoromethoxy)benzacetal then reacts with a substituted amine (for example, 4-amino-3,5-dichloropyridine), resulting in an N-substituted (3-cyclopropylmethoxy-4-difluoromethoxy)benzylimine. One of skill in the art will understand that a variety of substituted amines can be used in this process. The N-substituted (3-cyclopropylmethoxy-4-difluoromethoxy)benzylimine is then oxidized to afford the N-substituted (3-cyclopropylmethoxy- 4-difluoromethoxy)benzamide. In some embodiments, the N-substituted (3-cyclopropylmethoxy-4-difluoromethoxy) benzamide is roflumilast.

In some embodiments the present invention provides a process for preparing substituted benzamides as described above, wherein the compound of formula VIc is:

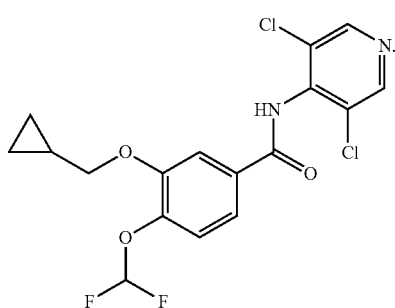

VIb

In some embodiments, the one-pot reaction converting IIc to Vc is conducted in conditions without using an aldehyde protecting reagent, wherein the one-pot reaction of step a) as discussed above, comprises contacting the compound of formula IIc

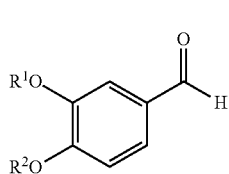

IIc with a compound of formula IVa

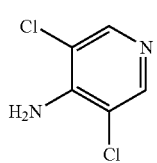

IVa in the presence of a catalyst and/or reaction promoter to form the compound of formula Vc In some embodiments, the aforesaid process is conducted in the presence of a catalyst such as Lewis acid and reaction promoter like silylation reagent. In some embodiments the inventive process as described above, wherein the Lewis acid including, but not limited to trimethylsilyl trifluoromethanesulfonate (TMSOTf), trimethylsilyl chloride (TMSCl), p-toluenesulfonic acid (PTSA), trifluoromethanesulfonic acid (TfOH), methanesulfonic acid (MSA), Trifluoroacetic acid (TFA) and mixture thereof and/or the silylation reagent is selected from N,O-Bis(trimethylsilyl)trifluoroacetamide (BSTFA), Bis(trimethylsilyl)acetamide (BSA) and mixture thereof.

In general, the reaction conditions, oxidants, and buffering agents contemplated for use in this related aspect are as described above. In some embodiments, the conversion of Vc to VIc is conducted in a mixture of tetrahydrofuran and water. In some embodiments, the compound of formula VIc is:

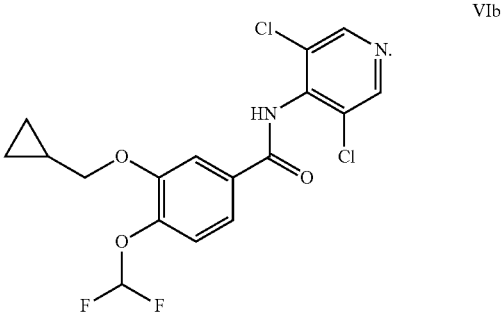 [SMILES: O=C(Nc1c(Cl)cncc1Cl)c1ccc(OC(F)F)c(OCC2CC2)c1]

VIb

In some embodiments, the present invention provides a process for preparing an N-substituted 3-cyclopropylmethoxy-4-difluoromethoxy benzamide by oxidation of the N-substituted imine obtained from a benzaldehyde and an aminopyridine. The molar ratio of the benzaldehyde to the aminopyridine is from 1:1 to 1:1.2. The amount of aminopyridine required is dramatically reduced as compared to known methods. For example, WO 2004/080967 requires a molar ratio of 1:1.8 to 1:2.7 for a benzaldehyde derivative and an aminopyridine. Therefore, the inventive process as presently disclosed is more economically efficient. In some embodiments, the invention provides a process for the conversion of a compound of formula below, to a compound of formula VIb, i.e. roflumilast. The compound of formula IIb can be made according to WO 2008/006509.

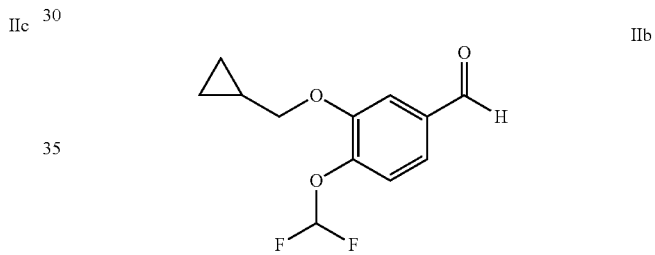

IIb

In some embodiments, the conversion process includes:
a) converting a compound of formula IIb in a one-pot reaction under conditions sufficient to provide a compound of formula IIIb

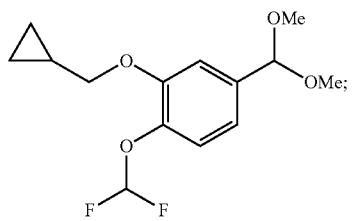

IIIb and
b) reacting the compound of formula IIIb with a compound of formula IVa

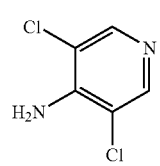

IVa in the one-pot reaction under conditions suitable to form a compound of formula Vb

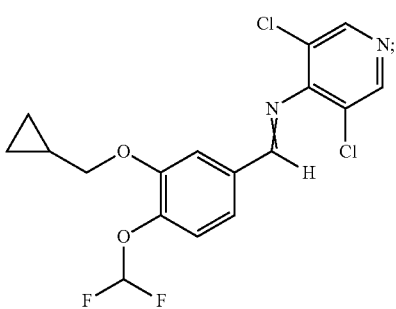

and c) oxidizing the compound of formula Vb to provide the compound of formula VIb.

In another aspect, the present invention provides a compound of formula Vc

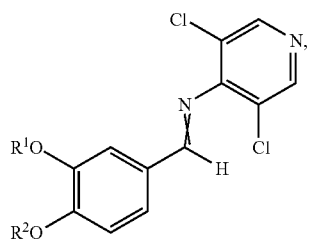

as well as a compound of formula IIIc

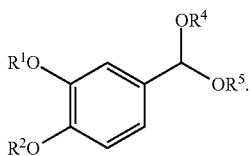

In some embodiments, the invention provides a compound of formula Vc:

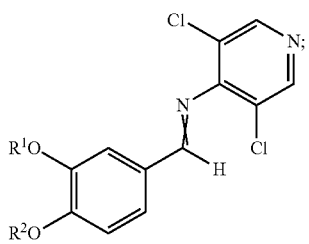

wherein:

R$^1$ and R$^2$ are independently selected from the group consisting of H; C$_{1-6}$ alkyl; C$_{3-7}$ cycloalkyl; C$_{3-7}$ cycloalkylmethyl; and C$_{1-4}$ alkyl which is partially or completely substituted with fluorine.

In some embodiments, the invention provides a compound of formula Vc wherein R$^1$ and R$^2$ are independently selected from the group consisting of C$_{3-7}$ cycloalkylmethyl and C$_{1-4}$ alkyl which is partially or completely substituted with fluorine.

In some embodiments, the compound of formula Vc has the formula:

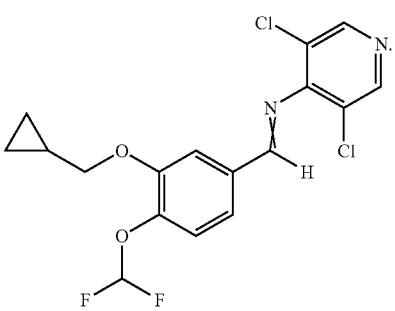

In some embodiments, the invention provides a compound of formula IIIc:

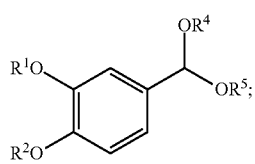

wherein:

R$^1$ are R$^2$ independently selected from the group consisting of H; C$_{1-6}$ alkyl; C$_{3-7}$ cycloalkyl; C$_{3-7}$ cycloalkylmethyl; and C$_{1-4}$ alkyl which is partially or completely substituted with fluorine; and R$^4$ and R$^5$ are independently selected from the group consisting of C$_{1-6}$ alkyl and acyl; or R$^4$ and R$^5$ are taken together to form an optionally substituted 5-7 member cyclic ring.

In some embodiments, the invention provides a compound of formula IIIc, wherein:

R$^1$ and R$^2$ are independently selected from the group consisting of C$_{1-6}$ alkyl; C$_{3-7}$ cycloalkylmethyl; and C$_{1-4}$ alkyl which is partially or completely substituted with fluorine; and R$^4$ and R$^5$ are independently selected from the group consisting of C$_{1-6}$ alkyl groups.

IV. Examples

The following examples are presented to describe the invention in further detail. However, the present invention is by no means restricted to the specific embodiments described herein.

Example 1

Synthesis of 3,5-dichloro-N-(3,4-dimethoxy)benzylidene)pyridin-4-amine (Va)

To a solution of 3,4-dimethoxybenzaldehyde (5 g, 30 mmol, 1.2 eq.) in toluene (25 mL) were added PTSA (103 mg, 0.6 mmol, 0.02 eq.) and TMOF (3.6 mL, 33 mmol, 1.32 eq.). The reaction mixture was heated to reflux for 2 hours and then cooled to 65±5° C. 4-Amino-3,5-dichloropyridine (4.1 g, 25 mmol, 1.0 eq.) and additional PTSA (413 mg, 2 mmol, 0.08 eq.) were added and the reaction mixture was then heated to 120° C. and refluxed for 15 hours. The mixture was cooled to room temperature and n-heptane (40 mL) was added. The precipitate was filtered, and the crude product was recrystallized from DCM/n-heptane to give 2.8 g of the imine as a colorless solid. $^1$H NMR (300 MHz, CDCl$_3$) δ 8.47 (s, 2H), 8.23 (s, 1H), 7.64 (s, 1H), 7.38 (d, 1H, J=8.4 Hz), 6.98 (d, 1H, J=8.4 Hz), 3.99 (s, 3H), 3.98 (s, 3H).

Example 2

Synthesis of N-(3,5-dichloro-pyridin-4-yl)-3,4-dimethoxy-benzamide (VIa)

The imine Va of Example 1 (311 mg, 1.0 mmol, 1.0 eq) was dissolved in a mixture of THF (5 mL) and 2-methylbut-2-ene (1.1 mL, 10.0 mmol, 10.0 eq). NaClO$_2$ (452 mg, 5.0 mmol, 5.0 eq) was then added to the solution. The reaction mixture was vigorously stirred while an aqueous solution of NaH$_2$PO$_4$ (3.3 M, 1.5 mL, 5.0 mmol, 5.0 eq) was added dropwise. When the reaction was complete as assessed by TLC, the reaction mixture was diluted with DCM (30 mL) and washed with water, 10% aqueous Na$_2$S$_2$O$_3$, and brine (10 mL each). The organic layer was dried over MgSO$_4$ and solvents were evaporated to afford the crude benzamide (283 mg). $^1$H NMR (300 MHz, CDCl$_3$) δ 8.57 (s, 2H), 7.69 (s, 1H), 7.54-7.52 (m, 3H), 6.97 (d, 1H, J=9.0 Hz), 6.97 (s, 6H).

Example 3

Synthesis of 3,5-dichloro-N-(3-(cyclopropyl-methoxy)-4-(difluoromethoxy)benzylidene)pyridin-4-amine (Vb)

To a solution of IIb (30 g, 123.9 mmol, 1.0 eq) in toluene (150 mL) at 20-30° C. under N$_2$ atmosphere were added trimethyl orthoformate (TMOF, 46.0 g, 433.7 mmol, 3.5 eq) and Amberlyst 15 wet (9.0 g, 30% w/w). The mixture was heated to reflux then kept refluxing until reaction completed. The solvent and excess TMOF were removed under reduced pressure at 50-60° C. to obtain IIIb. Toluene (150 mL) was added to the mixture and followed by the addition of IVa (21.2 g, 130.1 mmol, 1.05 eq) and TFA (2.8 g, 24.8 mmol, 0.2 eq) at a temperature of 40-50° C. The flask was connected with condenser and receiver, and the mixture was again heated to 110° C. and distillation was continued until the reaction was completed. The mixture was cooled to 50-60° C., then filtered and the solid was washed with toluene (30 mL). The filtrate was washed by saturated NaHCO$_3$ (60 mL) and water (60 mL), respectively. The organic phase was removed under reduced pressure (30-50 mmHg). The flask was charged with 95% EtOH (150 mL) and then 75 mL of solvent was distilled under reduced pressure at 50° C. Repeatedly, 75 mL of 95% EtOH was charged to the residue then 75 mL of solvent was distilled to afford Vb in EtOH solution. The mixture was cooled to 25° C. then additional 95% EtOH was charged to the residue to 210 mL followed by H$_2$O (90 mL) at the same temperature. The suspended solution was allowed to stirred for 30 min then cooled 0-5° C. then stirred for 1 hour. The slurry was filtered and the filter cake was washed with H$_2$O (30 mL) and dried under reduced pressure at 40° C. for 2 hours to obtain Vb (35 g, 73% yield).

MS m/z (M+1): 387.1;

IR (KBr): 3000, 2940, 1635, 1550, 1270, 1550$^{-1}$ cm.

$^1$H NMR (300 MHz, CDCl$_3$) δ 8.43 (s, 2H), 8.26 (s, 1H), 7.68 (s, 1H), 7.39-7.26 (m, 2H), 7.00-6.51 (t, 1H, J=75 Hz), 4.00 (d, 2H, J=6.9 Hz), 1.33 (m, 1H), 0.71-0.65 (m, 2H), 0.42-0.38 (m, 2H).

$^{13}$C NMR (125 MHz, CDCl$_3$) δ 165.38, 153.31, 150.98, 147.85, 144.15, 132.78, 124.23, 122.99, 122.29, 117.81 (CF$_2$, J$_{CF}$=260 Hz), 115.74 (CF$_2$), 113.66 (CF$_2$), 112.51, 74.01, 9.99, 3.22.

$^{19}$F NMR (282 MHz, CDCl$_3$) δ-82.24, −82.51.

Example 4

Synthesis of 3-(cyclopropylmethoxy)-N-(3,5-dichloro-pyridin-4-yl)-4-(difluoromethoxy) benzamide, (VIb; roflumilast).

Vb (24 g, 62.0 mmol, 1.0 eq.) was dissolved in a mixture of CH$_3$CN (96 mL) and 2-methyl-2-butene (17.5 g, 248.2 mmol, 4.0 eq.). Then 25% aqueous NaClO$_2$ [28.0 g (80% solid, 249 mmol) in 84 mL H$_2$O (4.0 eq)] was added in one portion. The mixture was placed into an ice-water bath. A solution of aqueous CH$_3$COOH [CH$_3$COOH (11.2 g, 186 mmol) diluted in H$_2$O (48 mL, 3.0 eq).] was added and the temperature was maintained below 25° C. The reaction mixture was vigorously stirred at 20-30° C. while product precipitated slowly as the reaction progressed. The reaction was stirred for 2 hours, 96 mL of H$_2$O was added and stirring was continued for 1 hour. The resulting slurry was filtered and the filter cake was washed with H$_2$O (36 mL). The product was dried under reduced pressure at 40° C. for 3 hours to obtain crude VIb, roflumilast (22.4 g, 92.4% yield with 98.0% purity).

Recrystallization of Roflumilast.

Crude roflumilast (10 g, 24.8 mmol) and CH$_3$CN (45 mL) were placed in a 250-mL reactor. The mixture was stirred and heated 65° C. to dissolve material. Insoluble material was removed by hot filtration. The mixture was heated to 70° C. then H$_2$O (22.3 mL) was added to the solution at the same temperature, then cooled down to 68±2° C. and held at that temperature for 2 hours. The mixture was cooled to 25±3° C. and continuously stirred at this temperature for 12 hours. The resulting crystals were collected by filtration, and the filter cake washed with H$_2$O (10 mL), dried at 40±2° C. under reduced pressure for 4 hours to get roflumilast (8.2 g, 82% yield with 99.7% purity).

MS m/z (M+1): 403.0

IR (KBr): 3445, 3262, 1651, 1503, 1156$^{-1}$ cm.

$^1$H NMR (300 MHz, CDCl$_3$) δ 8.58 (s, 2H), 7.66 (s, 1H), 7.59 (d, 1H, J=2.1 Hz), 7.49 (dd, 1H, J=2.1, 8.4 Hz), 7.31 (d, 1H, J=8.4 Hz), 7.00-6.50 (t, 1H, J=74.7 Hz), 3.98 (d, 2H, J=6.9), 1.4-1.2 (m, 1H), 0.70-0.67 (m, 2H), 0.39-0.37 (m, 2H).

$^{13}$C NMR (125 MHz, CDCl$_3$) δ 163.70, 150.99, 148.38, 143.94, 139.70, 130.88, 128.91, 122.36, 119.93, 117.76 (CF$_2$, J$_{CF}$=261 Hz), 115.68 (CF$_2$), 114.32, 113.66 (CF$_2$), 74.26, 10.02, 3.29.

$^{19}$F NMR (282 MHz, CDCl$_3$) δ-82.35, −82.62.

Example 5

Synthesis of N-(3,5-dichloro-pyridin-4-yl)-3,4-dimethoxy-benzamide (Va) via different acetals.

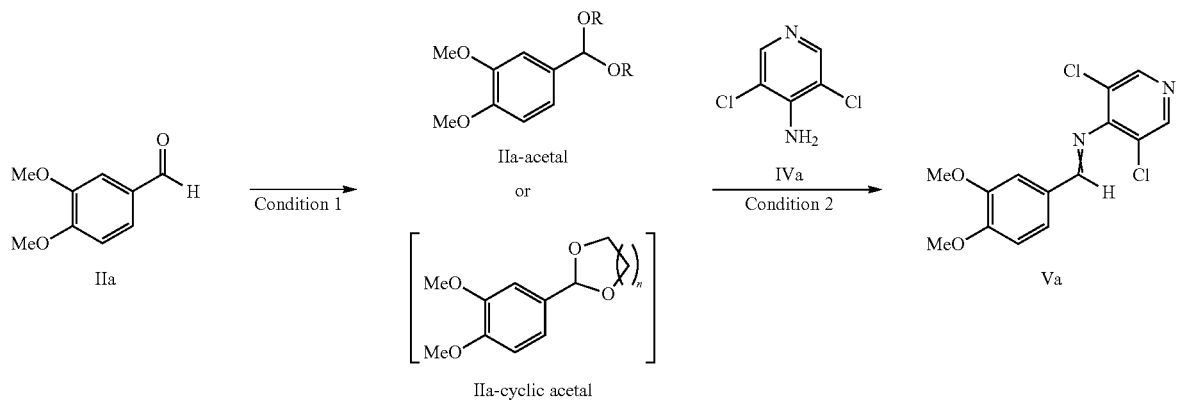

The compound of formula Va can be prepared from 3,4-dimethoxybenzaldehyde via different acetals. The experimental procedure in Example 1 is applied. The details of reagent and the results are summarized in Table 1.

TABLE 1

| | IIa to IIa-acetal or cyclic acetal | | IIa-acetal or IIa-cyclic acetal to Va | |
|---|---|---|---|---|
| Entry | Condition 1 | Result | Condition 2 | Result |
| 1 | IIa-acetal: R = Ac<br>IIa, Acetic anhydride, I$_2$, CH$_2$Cl$_2$ | Reaction was completed. | IVa, PTSA•H$_2$O, reflux | 43% of Va and 54% of IIa-acetal by HPLC |
| 2 | IIa-acetal: R = Et<br>IIa, TEOF, NH$_4$Cl, EtOH, reflux | Reaction was completed. | IVa, PTSA•H$_2$O, reflux | 87% of Va and 13% of IIa-acetal by HPLC |
| 3 | IIa- cyclic acetal: n = 2<br>IIa, propane-1,3-diol, PTSA•H$_2$O, toluene, reflux | Reaction was completed. | IVa, PTSA•H$_2$O, reflux for 33 hours | 5% of Va by LCMS |
| 4 | IIa- cyclic acetal: n = 1<br>IIa, ethane-1,2-diol, PTSA•H$_2$O, toluene, reflux | Reaction was completed. | IVa, PTSA•H$_2$O, reflux for 30 hours | 5% of Va by LCMS |

Example 6

Synthesis of N-(3,5-dichloro-pyridin-4-yl)-3,4-dimethoxy-benzamide (Va) without via acetal intermediates.

To a solution of 3,4-dimethoxybenzaldehyde (5 g, 30 mmol, 1.2 eq.) in toluene (25 mL) were added PTSA (103 mg, 0.6 mmol, 0.02 eq.) and 4-Amino-3,5-dichloropyridine (4.1 g, 25 mmol, 1.0 eq.). The reaction mixture was heated to reflux for 30 days. The mixture was cooled to room temperature and n-heptane (40 mL) was added. The precipitate was filtered, and the crude product was recrystallized from DCM/n-heptane to give 2.24 g of the imine as a colorless solid. $^1$H NMR (300 MHz, CDCl$_3$) δ 8.47 (s, 2H), 8.23 (s, 1H), 7.64 (s, 1H), 7.38 (d, 1H, J=8.4 Hz), 6.98 (d, 1H, J=8.4 Hz), 3.99 (s, 3H), 3.98 (s, 3H).

Example 7

Synthesis of 3,5-dichloro-N-(3-(cyclopropyl-methoxy)-4-(difluoromethoxy)benzylidene)pyridin-4-amine (Vb) without an acetal intermediate.

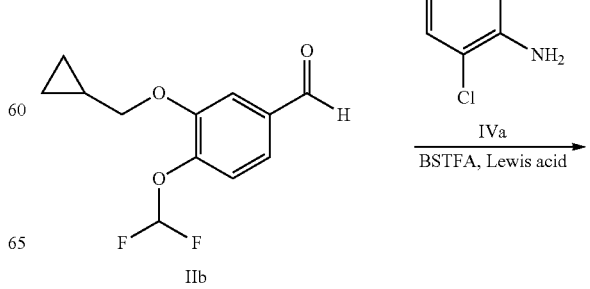

-continued

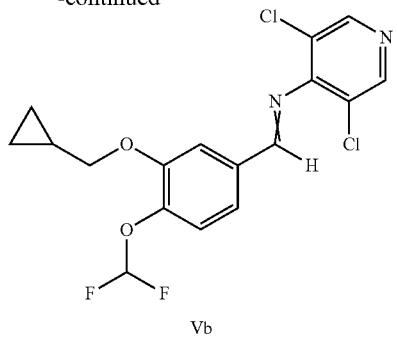

Vb

As is evident from the embodiment, the synthesis of the compound of formula IIb to the compound of formula Vb directly can be carried out with various Lewis acids in the presence of N,O-bis(trimethylsilyl)trifluoroacetamide (BSTFA). Table 2 shows the result using TMSOTf, TMSCl, PTSA, TfOH, MSA and TFA. The percentage of the convergence is observed via HPLC. The reaction is operated under conventional conditions in the presence of 0.2 equivalent of the Lewis acid. The reaction duration is from 3 to 48 hours.

TABLE 2

| Entry | Condition & materials | Vb HPLC purity |
|---|---|---|
| 1 | IVa, BSTFA, TMSOTf, $CH_3CN$, reflux for 3 h | 60% |
| 2 | IVa, BSTFA, TMSCl, $CH_3CN$, reflux for 24 h | 23% |
| 3 | IVa, BSTFA, PTSA, $CH_3CN$, reflux for 48 h | 70% |
| 4 | IVa, BSTFA, TfOH, $CH_3CN$, reflux for 5 h | 62% |
| 5 | IVa, BSTFA, MSA, $CH_3CN$, reflux for 20 h | 70% |
| 6 | IVa, BSTFA, TFA, $CH_3CN$, reflux for 18 h | 25% |

Example 8

Synthesis of N-(3,5-dichloro-pyridin-4-yl)-3,4-dimethoxy-benzamide (VIa) using different oxidation conditions.

As is evident from the embodiment, the oxidation of the compound of formula Va to the compound of formula VIa can be carried out with various oxidants. Table 3 shows the result using $KMnO_4$, m-CPBA, Oxone and TBHP. The percentage of the convergence is observed via HPLC. The reaction is operated under conventional oxidation conditions in the presence of 1-2 equivalents of oxidant. The reaction duration is from 1 to 24 hours.

TABLE 3

| | | Result | |
|---|---|---|---|
| Entry | Oxidant | Observed VIa by HPLC | Percentage (by HPLC) |
| 1 | $KMnO_4$ | ✓ | 27.5% |
| 2 | m-CPBA | ✓ | <2% |
| 3 | Oxone | ✓ | <2% |
| 4 | TBHP | ✓ | 9.7% |

Example 9

3-(cyclopropylmethoxy)-N-(3,5-dichloro-pyridin-4-yl)-4-(difluoromethoxy) benzamide (VIb) using different oxidation conditions.

As is evident from the embodiment, the oxidation of the compound of formula Vb to the compound of formula VIb can be carried out with various oxidants. Table 4 shows the result using $KMnO_4$, m-CPBA, Oxone and TBHP. The percentage of the convergence is observed via HPLC. The reaction is operated under conventional oxidation conditions in the presence of 1-2 equivalents of oxidant. The reaction duration is from 1 to 24 hours.

TABLE 4

| Entry | Condition & materials | Isolation yield |
|---|---|---|
| 1 | m-CPBA, $BF_3 \cdot Et_2O$, $CHCl_3$, rt | 28% |
| 2 | Oxone, $BF_3$—$Et_2O$, DMF | 32% |
| 3 | $KMnO_4$ (5.9 mmol), $CH_3CN/H_2O$, 50° C. | 65% |
| 4 | TBHP | <2% by HPLC |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of formula Vc:

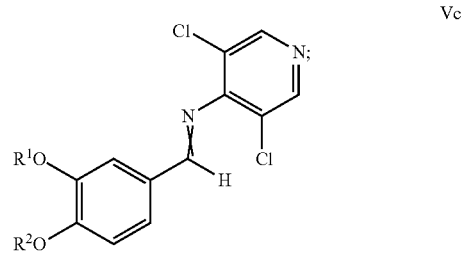

Vc wherein
R$^1$ and R$^2$ are independently selected from the group consisting of H; $C_{1-6}$ alkyl; $C_{3-7}$ cycloalkyl; $C_{3-7}$ cycloalkylmethyl; and $C_{1-4}$ alkyl which is partially or completely substituted with fluorine.

2. The compound of claim 1, wherein R$^1$ and R$^2$ are independently selected from the group consisting of $C_{3-7}$ cycloalkylmethyl and $C_{1-4}$ alkyl which is partially or completely substituted with fluorine.

3. A compound of claim 1, wherein the compound of formula Vc has the formula:

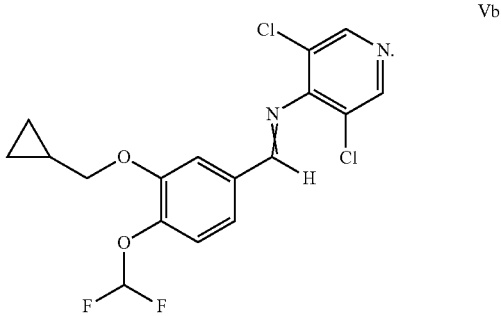 [SMILES: FC(F)Oc1ccc(C=Nc2c(Cl)cncc2Cl)cc1OCC1CC1]

Vb

* * * * *